United States Patent
Hatamori et al.

(12)

(10) Patent No.: US 6,535,943 B1
(45) Date of Patent: Mar. 18, 2003

(54) INFORMATION PROCESSING DEVICE ENABLING FLOATING INTERRUPT TO BE PENDING AND A METHOD EXECUTING AN INTERRUPT CONDITION CHANGE INSTRUCTION

(75) Inventors: Syuuei Hatamori, Kanagawa (JP); Aiichiro Inoue, Kanagawa (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/533,034

(22) Filed: Mar. 22, 2000

(30) Foreign Application Priority Data

Sep. 30, 1999 (JP) ............................................ 11-278006

(51) Int. Cl.$^7$ ................................................ G06F 13/24
(52) U.S. Cl. ...................................... 710/261; 370/223
(58) Field of Search ................................ 710/260–269; 370/223

(56) References Cited

U.S. PATENT DOCUMENTS

| | | | | |
|---|---|---|---|---|
| 5,261,054 A | * | 11/1993 | Lerner et al. ................ | 345/157 |
| 5,581,770 A | * | 12/1996 | Suzuki ........................ | 710/220 |
| 5,640,571 A | * | 6/1997 | Hedges et al. ............... | 710/260 |
| 5,708,814 A | * | 1/1998 | Short et al. .................. | 710/260 |
| 6,091,705 A | * | 7/2000 | Regula ........................ | 370/223 |
| 6,279,067 B1 | * | 8/2001 | Callway et al. .............. | 710/260 |

FOREIGN PATENT DOCUMENTS

| | | |
|---|---|---|
| JP | 60-150140 | 8/1985 |
| JP | 6-59919 | 3/1994 |
| JP | 6-187178 | 7/1994 |
| JP | 6-250849 | 9/1994 |
| JP | 8-214209 | 9/1996 |

* cited by examiner

Primary Examiner—Rupal Dharia
(74) Attorney, Agent, or Firm—Staas & Halsey, LLP

(57) ABSTRACT

An information processing device, which includes a plurality of CPUs, and can make a floating interrupt as an interrupt that can be executed by any of the plurality of CPUs pending, comprises an interrupt pending signal generating unit always transmitting a pending interrupt signal that indicates the presence/absence of a pending floating interrupt to each of the CPUs, and an interrupt condition change instruction execution controlling unit, which is comprised by each of the CPUs, making its own CPU execute the interrupt condition change instruction.

9 Claims, 15 Drawing Sheets

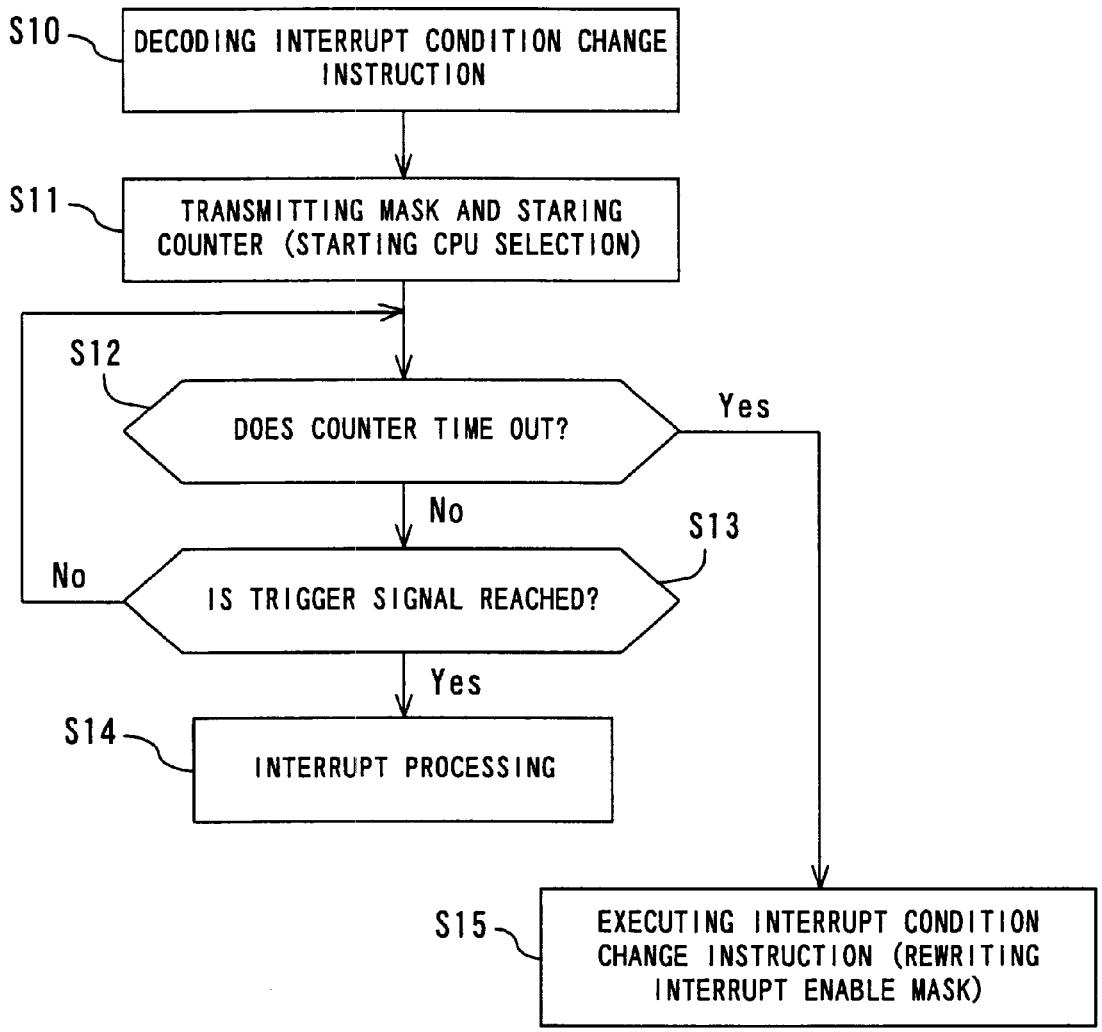
F I G. 2

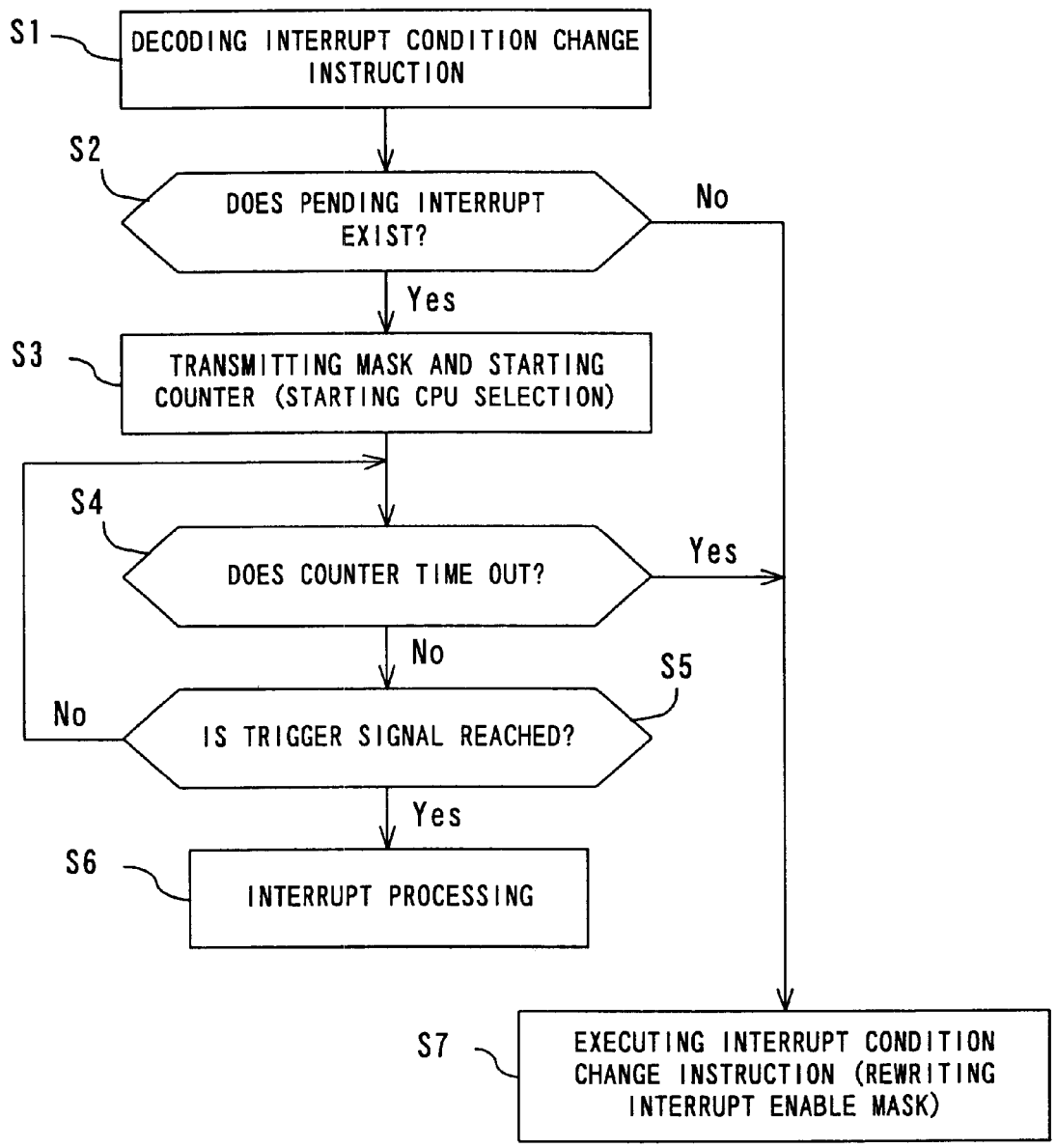
F I G. 6

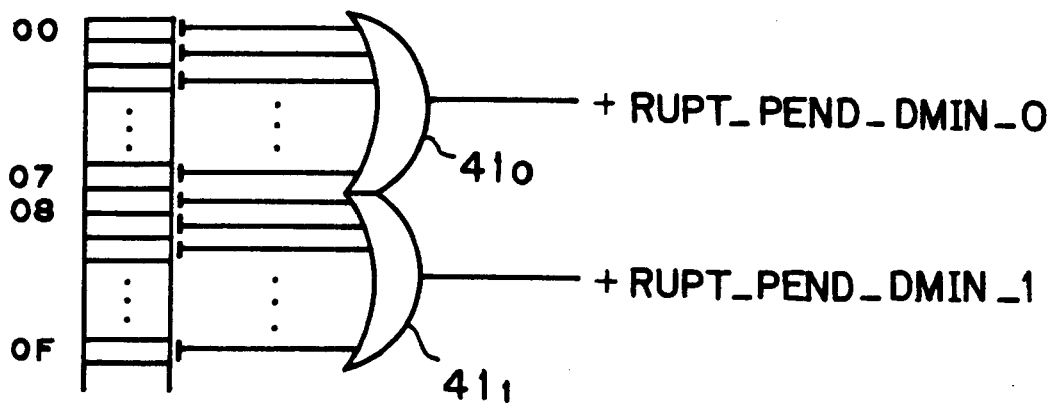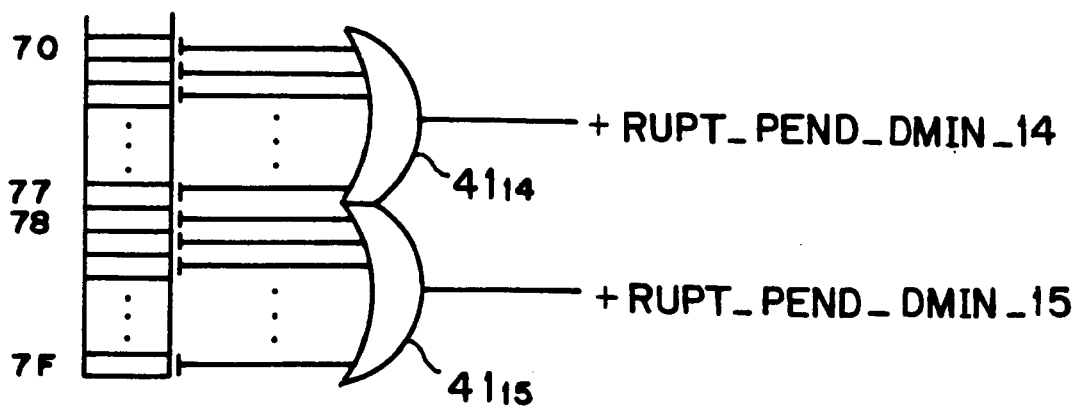
FIG. 13

INFORMATION PROCESSING DEVICE ENABLING FLOATING INTERRUPT TO BE PENDING AND A METHOD EXECUTING AN INTERRUPT CONDITION CHANGE INSTRUCTION

BACKGROUND OF THE INVENTION

1. Field of the Invention

The present invention relates to an information processing device comprising a plurality of CPUs, and more particularly, to an information processing device which immediately executes an interrupt condition change instruction if no pending floating interrupt as an interrupt that can be executed by any of the plurality of CPUs exists.

2. Description of the Related Art

In an information processing device comprising a plurality of CPUs, there are various methods in the case where one or the plurality of CPUs are made to execute interrupt processing. For example, the case where a particular CPU is specified and made to execute interrupt processing, the case of a broadcast interrupt that makes all of the CPUs execute interrupt processing, the case of a floating interrupt (an event-like interrupt) that may make any of the plurality of CPUs execute interrupt processing, or the like. The present invention targets an information processing device which makes the above described floating interrupt pending.

Normally, interrupt processing is not immediately executed in all cases, and its execution is sometimes made pending. Assume that one of a plurality of CPUs decodes an interrupt condition change instruction within a program, and this instruction is attempted to be executed. This interrupt condition change instruction is, for example, an instruction which changes an interrupt enable mask to be described later.

Normally, when this interrupt condition change instruction is executed, whether or not an interrupt to be processed under a current interrupt condition is pending is examined within an information processing device. If the interrupt to be processed is pending, this instruction is executed after the interrupt processing is executed. If the interrupt to be processed is not pending, the instruction is immediately executed.

A conventional method for processing such a pending floating interrupt will be described below by taking an input/output interrupt as an example of a floating interrupt. FIG. 1 is a block diagram showing the fundamental configuration of an information processing device for an explanation of pending input/output interrupt processing. In this figure, the information processing device comprises an IOP (Input/Output Processor) 50, an MCU (Memory Control Unit) controlling a storage device such as a main storage, etc., and a plurality of CPUs (Central Processing Units) $52_0$ to $52_n$. The CPUs $52_0$ to $52_n$ respectively include instruction controlling units $53_0$ to $53_n$ controlling instructions within the respective CPUs.

In FIG. 1, an input/output interrupt, for example, an interrupt corresponding to each of a plurality of input/output channels is transmitted from the IOP 50 to the MCU 51 as a floating interrupt, for example, along with the signal indicating that the interrupt is pending. Within the MCU 51, data indicating whether or not a floating interrupt is pending is stored in correspondence with each of the channels in a pending latch to be described later.

An interrupt condition change instruction changing an interrupt condition is decoded, for example, by one of the plurality of CPUs $52_0$ to $52_n$, and the need for executing this instruction arises. A floating interrupt may be executed by any of the CPUs as described above. Therefore, each of the instruction controlling units $53_0$ to $53_n$ within each of the CPUs transmits to the MCU 51 an interrupt enable mask stored therein, that is, the value of the mask indicating whether or not an interrupt is enabled for its CPU in correspondence with each of the input/output channels.

Since the interrupt enable mask and the above described pending latch store the data corresponding to each of the channels one by one, the MCU transmits an interrupt processing request signal (trigger signal) to the instruction controlling unit within the CPU whose mask value of the input/output channel corresponding to the pending interrupt is, for example, 1, and whose priority is the highest. The CPU controlled by the instruction controlling unit starts the interrupt processing upon receipt of the trigger signal.

FIG. 2 is a flowchart showing a conventional interrupt condition change instruction process. Once the process is started in this figure, an interrupt condition change instruction is first decoded, for example, by a certain CPU in step S10 and the need for executing this instruction arises. Then, an interrupt enable mask is transmitted from the instruction controlling unit in each of the CPUs to the MCU in step S11. If a pending floating interrupt exists, the process for selecting a CPU made to execute this interrupt and for transmitting a trigger signal to the selected CPU is started prior to the execution of the interrupt condition change instruction on the MCU side.

In the instruction controlling unit in each of the CPUs, a counter, for example, a process wait counter to be described later, is started in order to wait for a trigger signal which can possibly be transmitted from the MCU side, when the interrupt enable mask is transmitted in step S11, and whether or not the counter times out is determined in step S12. If the counter does not time out, whether or not the trigger signal is reached is determined in step S13. If the trigger signal is not reached, the operations in and after step S12 are repeated.

If the trigger signal is determined to be reached in step S13 before the counter does not time out in step S12, the pending interrupt is processed by the CPU which has received the trigger signal, that is, the selected CPU. In the unselected CPUs, the interrupt condition change instruction in step S15 is executed when the counter is determined to time out in step S12, and, for example, the interrupt enable mask stored in the instruction controlling unit is rewritten.

FIG. 3 is a block diagram showing the configuration of the information processing device in which the configuration of the MCU is especially illustrated in detail. Processing for a pending floating interrupt in this figure will be explained below. In this figure, an IO rupture (RUPT) ID (7 bits+parity check bit P) signal (+IO_RUPT_ID) indicating to which one of for example, 128 input/output channels an interrupt corresponds is transmitted from the IOP 50 to the MCU 51 along with a signal (+SET_PENDING) making an IO (Input/Output) interrupt pending in (1). These values are once stored in a 10-bit latch 70. Then, the value of the IO rupture ID by a decoder 71, and the bit corresponding to the input/output channel for which an interrupt is made pending is assumed to be "1" among four pending latches $72_1$ to $72_4$ of 32 bits respectively corresponding to the 128 channels in (2).

When one CPU decodes an interrupt condition change instruction and the need for executing the decoded instruction arises, the contents (128 bits) of the IO rupture masks $79_0$ to $79_{15}$ indicating whether or not an interrupt corresponding to the respective input/output channels is enabled are serially transferred, for example, by 4 bits in 32 time divisions by the instruction controlling unit within each of the CPUs. This serial transfer is not limited particularly to 32 time divisions.

A priority circuit 75, which selects the CPU made to process a pending floating interrupt as described above within the MCU 51, makes a comparison between the interrupt enable mask transmitted from the CPU side and the contents stored in the pending latches, and determines whether or not an interrupt by each of the CPUs is enabled for the pending floating interrupt. Accordingly, the contents stored in the respective pending latches $72_1$ to $72_4$ are serially transferred to the priority circuit 75 via selectors $73_1$ to $73_4$ according to the selection control of a mask select counter. Here, the mask select counter is a counter for this time division transfer, and does not always mean a mask selection.

The priority circuit 75 makes a comparison between the contents stored in the pending latches and the interrupt enable mask transmitted from the CPU side, and selects the CPU which is in a wait state and physically has a smaller component number under the same condition from among CPUs for which an interrupt is enabled as a CPU made to process a pending interrupt. Here, the information of the CPU in the wait state is provided to the priority circuit 75 as a CPU wait state in signal (CPU_WAIT_STATE_IN) in (5).

The priority circuit 75 provides a trigger signal (IO_RUPT_TGR) and an IO rupture ID signal (IO_RUPT_ID) (8 bits including a parity check bit P) corresponding to an input/output channel number to one of latches $76_0$ to $76_{15}$ which correspond to the CPUs $52_0$ to $52_{15}$ one by one. Its contents are transmitted to the CPU side via any of latches $77_0$ to $77_{15}$ by the selection control of the mask select counter, for example, by using a serial transfer in 16 time divisions according to the selection control of a mask selection counter in (6). The transmitted signal is stored in any of latches $78_0$ to $78_{15}$ within the instruction controlling unit on the CPU side, and used to process the pending interrupt.

Upon completion of the interrupt process on the CPU side, a reset rupture pending signal (RESET_RUPT_PENDING) and a reset rupture trigger signal (RESET_RUPT_TRG) are serially transferred to the MCU 51, for example, in 16 time divisions as a cancel signal (CPU_IO_RUPT_CNTL_IN) in (7), and the corresponding bits within the pending latches $72_1$ to $72_4$ and within the latches $76_0$ to $76_{15}$ corresponding to the respective CPUs are reset.

As described above, with the conventional pending interrupt processing method, a trigger signal transmitted from the MCU side must be waited to determine whether or not there is an interrupt to be processed by a corresponding CPU after the instruction controlling unit in each CPU transmits an interrupt enable mask to the MCU side. Since the MCU side transmits a trigger signal only to the CPU made to process the pending interrupt, even the CPUs which are not required to execute the pending interrupt must wait until a counter times out as explained in step S12.

In the first place, even if no pending floating interrupts exist on the MCU side, all of the CPUs cannot execute an interrupt condition change instruction until a timer times out. That is, each CPU spends a useless wait time, for example, whenever an instruction rewriting an interrupt enable mask is decoded on the CPU side, which leads to a performance degradation of an information processing device.

SUMMARY OF THE INVENTION

An object of the present invention is to speed up the processing for an interrupt condition change instruction by eliminating the need for spending a useless wait time if no pending floating interrupts exist or if no pending interrupt to be executed by a corresponding CPU exists, in an information processing device which comprises a plurality of CPUs, inquires of an MCU as to whether or not a floating interrupt which can be executed by any of the plurality of CPUs is pending, when a certain CPU decodes an interrupt condition change instruction, and executes the interrupt condition change instruction when there is no instruction for a pending floating interrupt to the corresponding CPU.

An information processing device according to the present invention comprises a plurality of CPUs, and can make a floating interrupt as an interrupt which can be executed by any of the plurality of CPUs pending. This information processing device comprises an interrupt pending signal generating unit which always transmits a signal indicating the presence/absence of a pending floating interrupt to the plurality of CPUs; and an interrupt condition change instruction execution controlling unit which is comprised by each of the CPUS, and immediately makes its own CPU execute an interrupt condition change instruction when the interrupt condition change instruction is issued and the output of the interrupt pending signal generating unit indicates the absence of a pending interrupt.

With such a configuration, a CPU can immediately execute an interrupt condition change instruction on the condition that no pending floating interrupts exist when the interrupt condition change instruction is issued, thereby improving the performance of the information processing device.

BRIEF DESCRIPTION OF THE DRAWINGS

FIG. 2 shows a conventional example of the process flowchart for an interrupt condition change instruction;

FIG. 6 is a flowchart showing the process for an interrupt condition change instruction in the first preferred embodiment;

FIG. 13 exemplifies the configuration of an each domain interrupt pending signal generating circuit;

DESCRIPTION OF THE PREFERRED EMBODIMENTS

Figure 1:
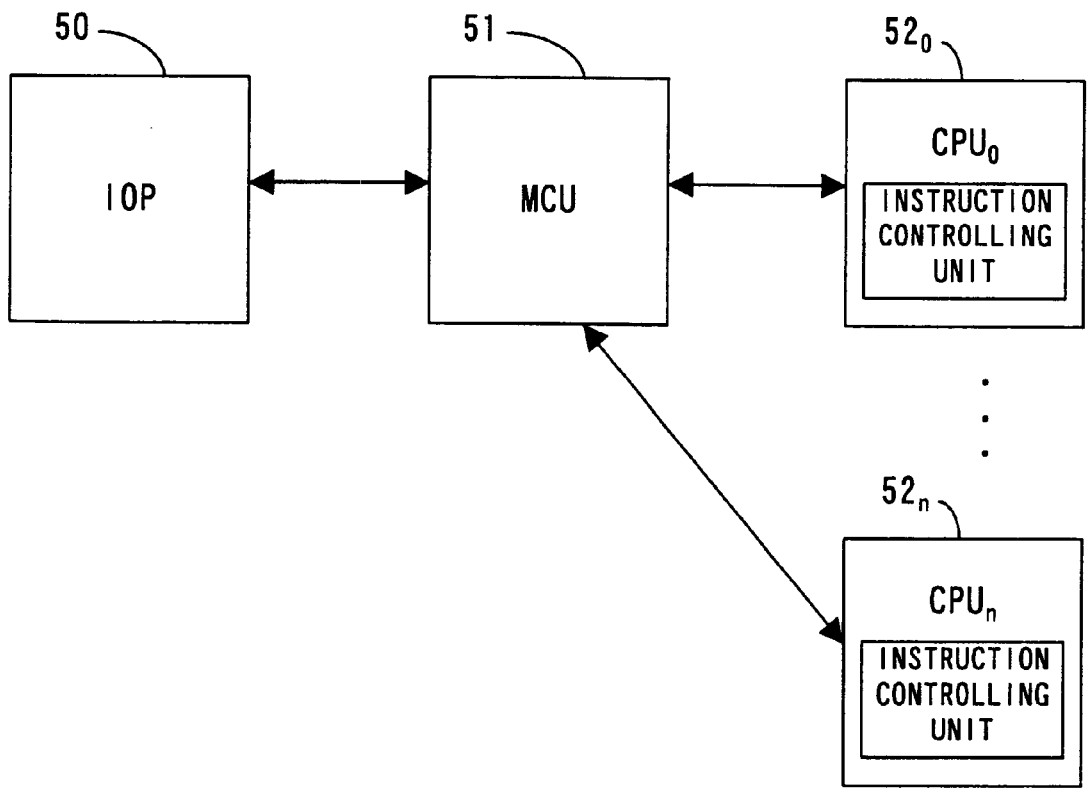
FIG. 1 is a block diagram showing the fundamental configuration of an information processing device targeted by the present invention.

Hereinafter, the present invention will be described in detail by referring to the drawings.

Figure 4B:
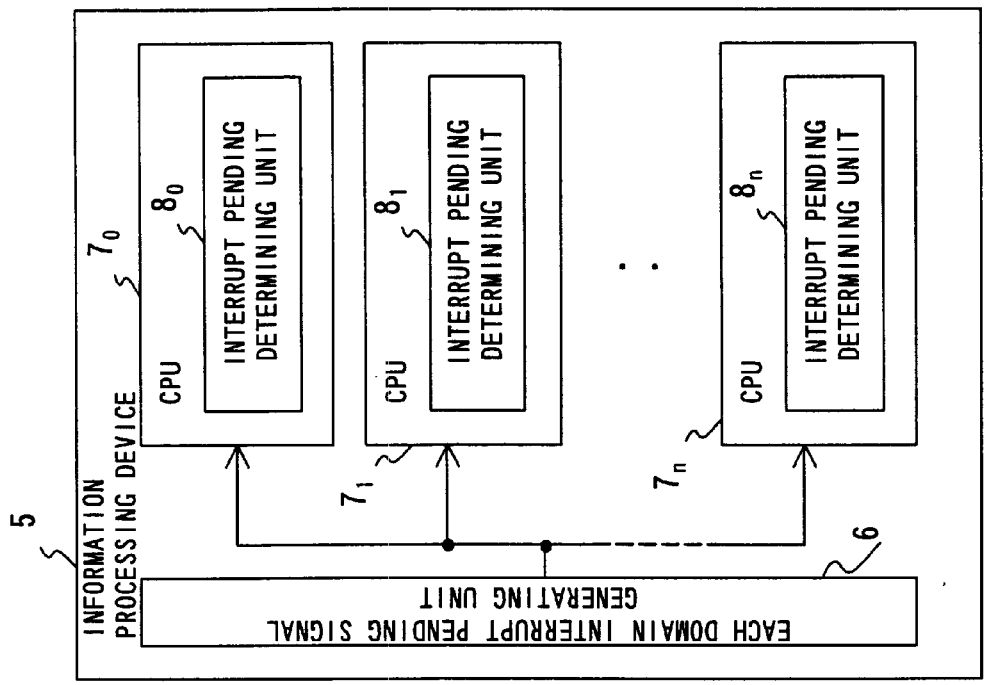
FIG. 4B is a block diagram showing the principle of a second preferred embodiment according to the present invention.
Figure 4A:
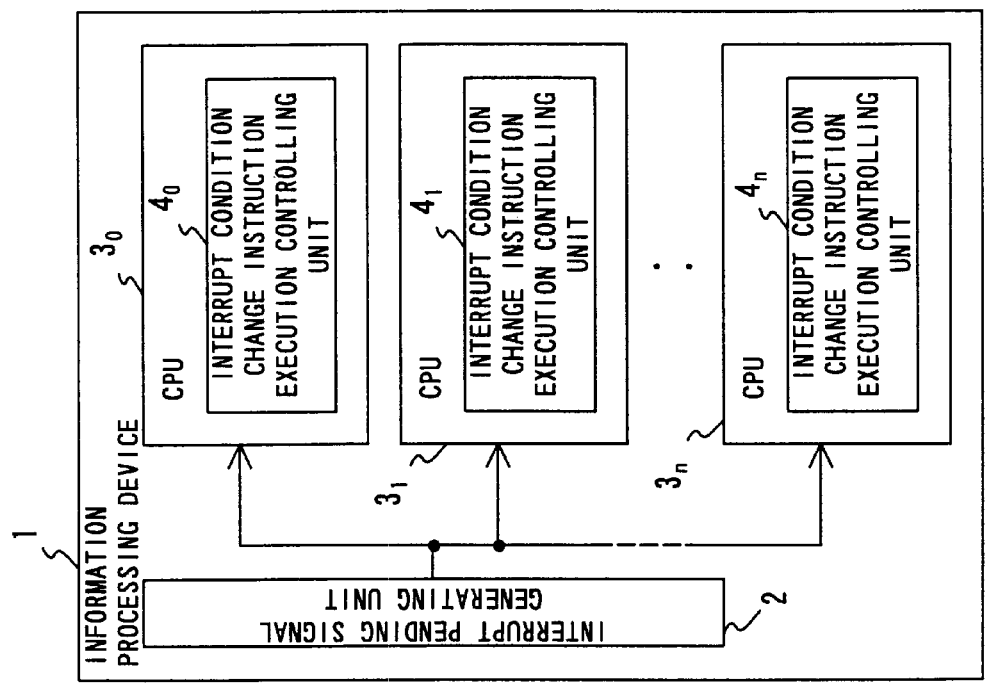
FIG. 4A is a block diagram showing the principle of a first preferred embodiment according to the present invention.

FIGS. 4A and 4B are block diagrams showing the principles of the present invention. FIG. 4A is a block diagram showing the principle of the first preferred embodiment to be described later, and shows the principle of an information processing device 1 which comprises a plurality of CPUs, and can make a floating interrupt as an interrupt which can be executed by any of the CPUs pending.

In FIG. 4A, an interrupt pending signal generating unit 2 is arranged, for example, within a memory controlling unit, and always transmits the signal indicating the presence/absence of a pending floating interrupt to a plurality of CPUs $3_0$ to $3_n$.

Interrupt condition change instruction execution controlling units $4_0$ to $4_n$ are arranged within the respective CPUs $3_0$ to $3_n$, and intended to perform a control for making their own CPUs immediately execute an interrupt condition change instruction when the interrupt condition change instruction is issued and the signal transmitted form the interrupt pending signal generating unit 2 indicates the absence of a pending interrupt.

Available as the method executing an interrupt condition change instruction according to the first preferred embodiment is a method receiving a signal which indicates the presence/absence of a pending floating interrupt and is always transmitted, and immediately executing an interrupt condition change instruction when this instruction is issued and the above described signal indicates the absence of a pending interrupt.

Furthermore, in the first preferred embodiment, a computer-readable portable storage medium on which is recorded a program for causing a computer to perform a process comprising: receiving a signal which indicates the presence/absence of a pending floating interrupt and is always transmitted; and immediately executing an interrupt condition change instruction when the interrupt condition change instruction is issued and a transmitted signal indicates the absence of a pending interrupt, is available as a storage medium for use in an information processing device which can make a floating interrupt pending.

As described above, in the first preferred embodiment according to the present invention, each CPU can immediately execute an interrupt condition change instruction if no pending floating interrupts exist in an information processing device which comprises a plurality of CPUs and can make a floating interrupt pending. This interrupt condition change instruction is an instruction which changes an interrupt enable mask indicating whether or not an interrupt for an input/output channel is enabled for a corresponding CPU, for example, in correspondence with a plurality of input/output channels. If no pending floating interrupts exist, an interrupt condition change instruction can be immediately executed when being issued without waiting for a trigger signal as an interrupt processing request signal transmitted, for example, from an MCU as conventional.

FIG. 4B is a block diagram showing the principle of the second preferred embodiment according to the present invention. This figure shows the principle of an information processing device 5 which comprises a plurality of CPUs to which domains as resources such as a CPU, a memory, etc. are allocated in correspondence processing, and can make a floating interrupt as an interrupt which can be executed by any of the plurality of CPUs pending.

In FIG. 4B, an each domain interrupt pending signal generating unit 6 is arranged, for example, within a memory controlling unit, and always transmits the signal indicating the presence/absence of a pending floating interrupt to a plurality of CPUs $7_0$ to $7_n$ in correspondence with respective domains.

Pending interrupt determining units $8_0$ to $8_n$ are respectively arranged within the plurality of CPUs $7_0$ to $7_n$, and determine the presence/absence of a pending floating interrupt for domains to which their own CPUs are allocated by using the signal from the each domain interrupt pending signal generating unit 6.

In the second preferred embodiment, each of the CPUs may further comprise an interrupt condition change instruction execution controlling unit. The interrupt condition change instruction execution controlling unit performs a control for making its own CPU immediately execute an interrupt condition change instruction when this instruction is issued and the pending interrupt determining unit determines the absence of a pending interrupt for the domain to which its own CPU is allocated.

Available as the method executing an interrupt condition change instruction according to the second preferred embodiment is a method receiving a signal which indicates the presence/absence of a pending floating interrupt in correspondence with each domain and is always transmitted, determining the presence/absence of a pending floating interrupt for a domain to which a corresponding CPU is allocated by using the received signal, and immediately executing an interrupt condition change instruction when this instruction is issued and no pending interrupt for the domain to which the corresponding CPU is allocated is determined to exist as a result of the determination.

Furthermore, also available as a storage medium for use in an information processing device which can make a floating interrupt pending according to the second preferred embodiment is a computer-readable portable storage medium on which is recorded a program for causing a computer to perform a process comprising: receiving a signal which indicates the presence/absence of a pending floating interrupt in correspondence with each domain, and is always transmitted; determining the presence/absence of a pending floating interrupt for a domain to which a corresponding CPU is allocated by using the received signal; and immediately executing an interrupt condition change instruction when this instruction is issued and no pending interrupt for the domain to which the corresponding CPU is allocated is determined to exist as a result of the determination.

As described above, in the second preferred embodiment according to the present invention, domains are allocated to a plurality of CPUs in correspondence with processing. Therefore, even if a floating interrupt for a domain other than a domain to which a corresponding CPU is allocated is pending, there is no need to wait for an interrupt processing request signal, that is, a trigger signal when an interrupt condition change instruction is issued. Accordingly, if no pending floating interrupt for the domain to which a corresponding CPU is allocated is proved to exist according to the signal from the each domain interrupt pending signal generating unit 6, an interrupt condition change instruction can be executed immediately when this instruction is issued.

Figure 5:
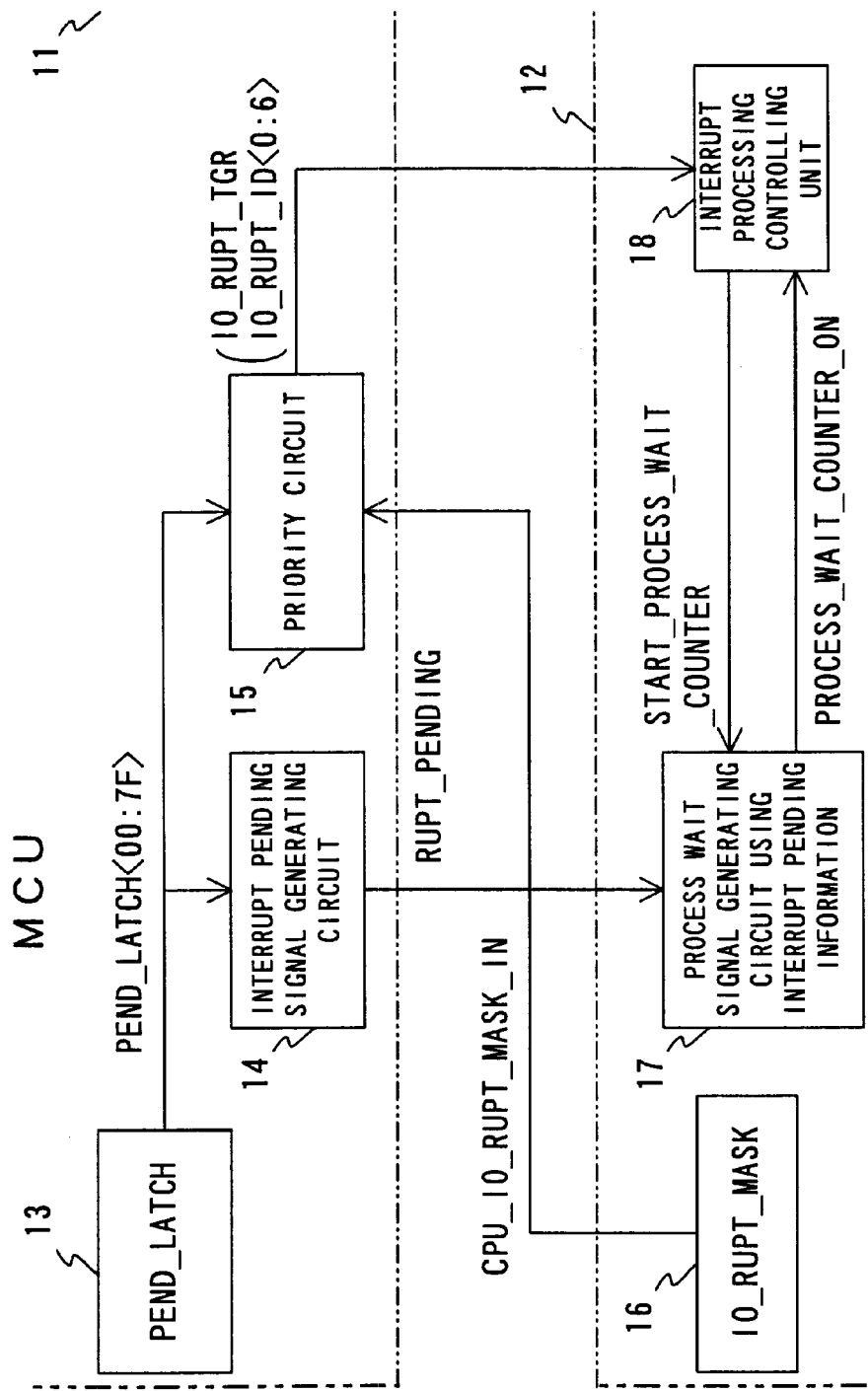
FIG. 5 is a block diagram showing the fundamental configuration of the information processing device according to the first preferred embodiment of the present invention.

FIG. 5 is a block diagram showing the fundamental configuration of the information processing device according to the first preferred embodiment. In this figure, the IO processor shown in FIG. 1 is omitted, and only one of the plurality of CPUs is shown.

In this figure, an MCU (Memory Control Unit) 11 includes an interrupt pending signal generating circuit 14 specific to the present invention in addition to a pending latch 13 and a priority (determining) circuit 15, which are described earlier by referring to FIG. 3. The interrupt pending signal generating circuit 14 generates a signal which is stored in the pending latch 13, and indicates whether or not a floating interrupt is pending in correspondence with the 128 input/output channels in FIG. 3, and outputs the generated signal to a CPU 12 side as a rupture pending signal (RUPT_PENDING). Additionally, an IO rupture trigger signal (IO_RUPT_TGR) and an IO rupture ID signal (IO_RUPT_ID) are output from the priority circuit 15 to the CPU made to process a pending interrupt as described above.

The CPU 12 includes an IO rupture mask latch 16 storing an interrupt enable mask, a process wait signal generating circuit 17 using interrupt pending information, and an interrupt processing controlling unit 18.

If an interrupt condition change instruction is decoded by one CPU and its execution becomes necessary, the interrupt processing controlling unit 18 outputs a start process wait counter signal (START_PROCESS_WAIT_COUNTER) to the process wait signal generating circuit 17 using the interrupt pending information. According to this signal, a process wait counter within the process wait signal generating circuit 17, which will be described later, starts its operations using the interrupt pending information.

If the rupture pending signal (RUPT_PENDING) input from the MCU 11 side indicates that a pending floating interrupt is stored on the MCU 11 side, the process wait signal generating circuit 17 using the interrupt pending information outputs a process wait counter on signal (PROCESS_WAIT_COUNTER_ON), which indicates that the process wait counter is running, to the interrupt processing controlling unit 18.

Furthermore, at this time point, the contents of the IO rupture mask 16 are transmitted to the priority circuit 15 within the MCU 11 as a CPU IO rupture mask in signal (CPU_IO_RUPT_MASK_IN). The priority circuit 15 determines the CPUs which can be made to process a pending floating interrupt by making a comparison between the transmitted signal and the contents stored in the pending latch 13 as described above, selects one from among the determined CPUs according to their priorities, and makes the selected CPU execute the pending interrupt processing by transmitting the IO rupture trigger signal (IO_RUPT_TGR) and the IO rupture ID signal (IO_RUPT_ID) to this CPU.

As described above, the process wait counter is started the same time an interrupt condition change instruction is decoded. This counter continues to run while the contents of the interrupt enable mask are transmitted ($t_1$), the presence/absence of a pending interrupt to be processed is determined on the MCU 11 side ($t_2$), a trigger signal is transmitted from the MCU 11 to a selected CPU 12 ($t_3$), and the CPU 12 receives the trigger signal ($t_4$), that is, a time period of $$T=t_1+t_2+t_3+t_4.$$

The CPU 12 side waits for the trigger signal from the MCU 11 while the process wait counter on signal is being input to the interrupt processing controlling unit 18, that is, while the counter times out, and executes the pending interrupt processing upon completion of the input of the trigger signal. However, if the process wait counter times out in the state where the trigger signal is not reached, the process wait counter on signal is not input. As a result, the interrupt condition change instruction can be executed at this time point.

Furthermore, when no pending floating interrupts for all of the input/output channels are determined to exist according to the rupture pending signal provided from the MCU Side, the process wait counter on signal is not output from the process wait signal generating circuit 17 using the interrupt pending information to the interrupt processing controlling unit 18. Consequently, the interrupt processing controlling unit 18 can execute the interrupt condition change instruction immediately after outputting the start process wait counter signal.

The above provided explanation refers to the case where the number of pending interrupts to be processed is only one. However, a similar control is performed also in the case where two or more interrupts are pending.

FIG. 6 is a flowchart showing the process for an interrupt condition change instruction in the first preferred embodiment according to the present invention. Comparing this figure with the conventional example shown in FIG. 2, there is a fundamental difference in that whether or not pending floating interrupts exist is determined according to the rupture pending signal described by referring to FIG. 5 in step S2, and an interrupt condition change instruction is immediately executed if no pending interrupts are determined to exist, in step S7.

Figure 3:
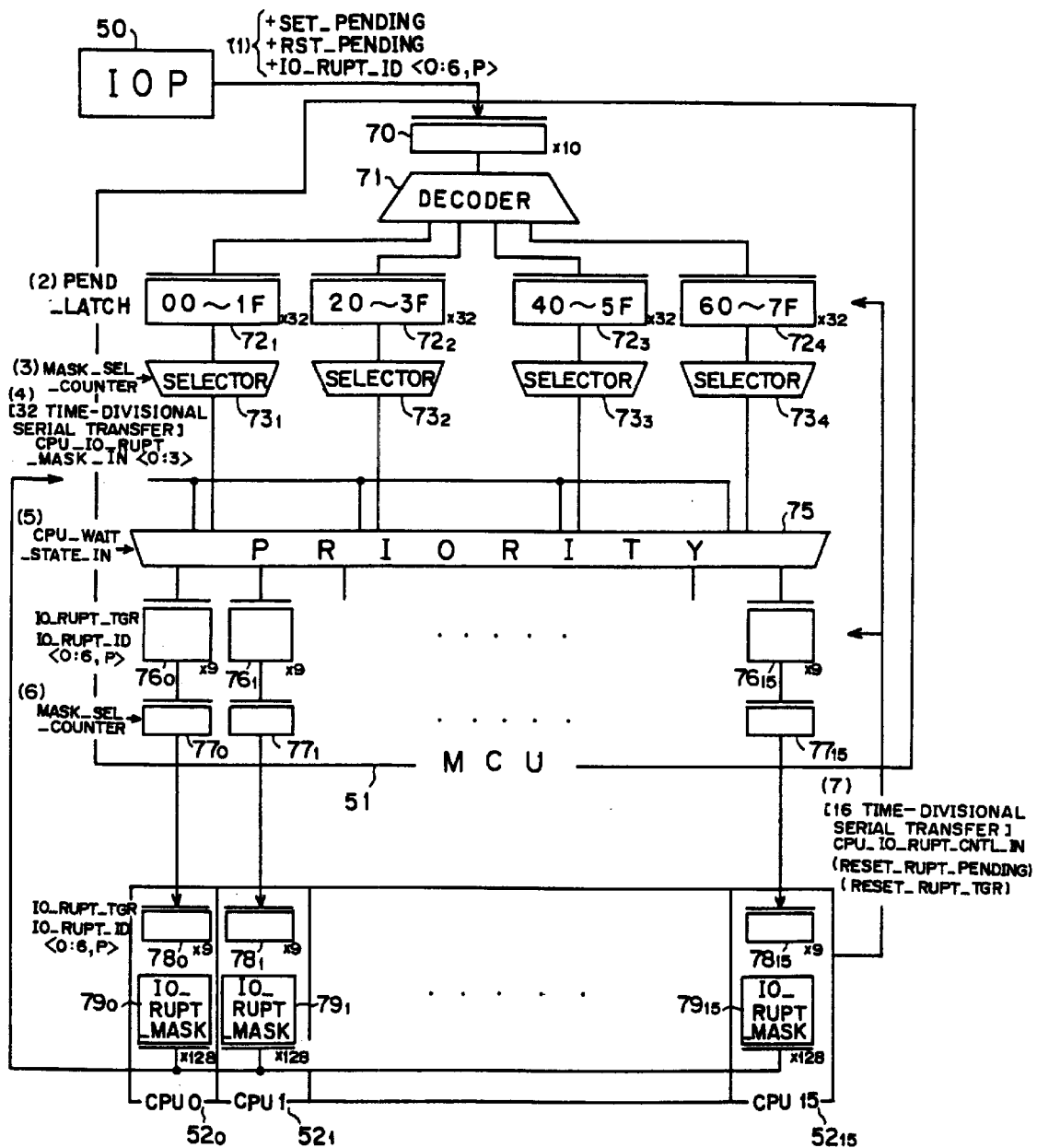
FIG. 3 is a block diagram showing the detailed configuration of a conventional information processing device example.
Figure 7:
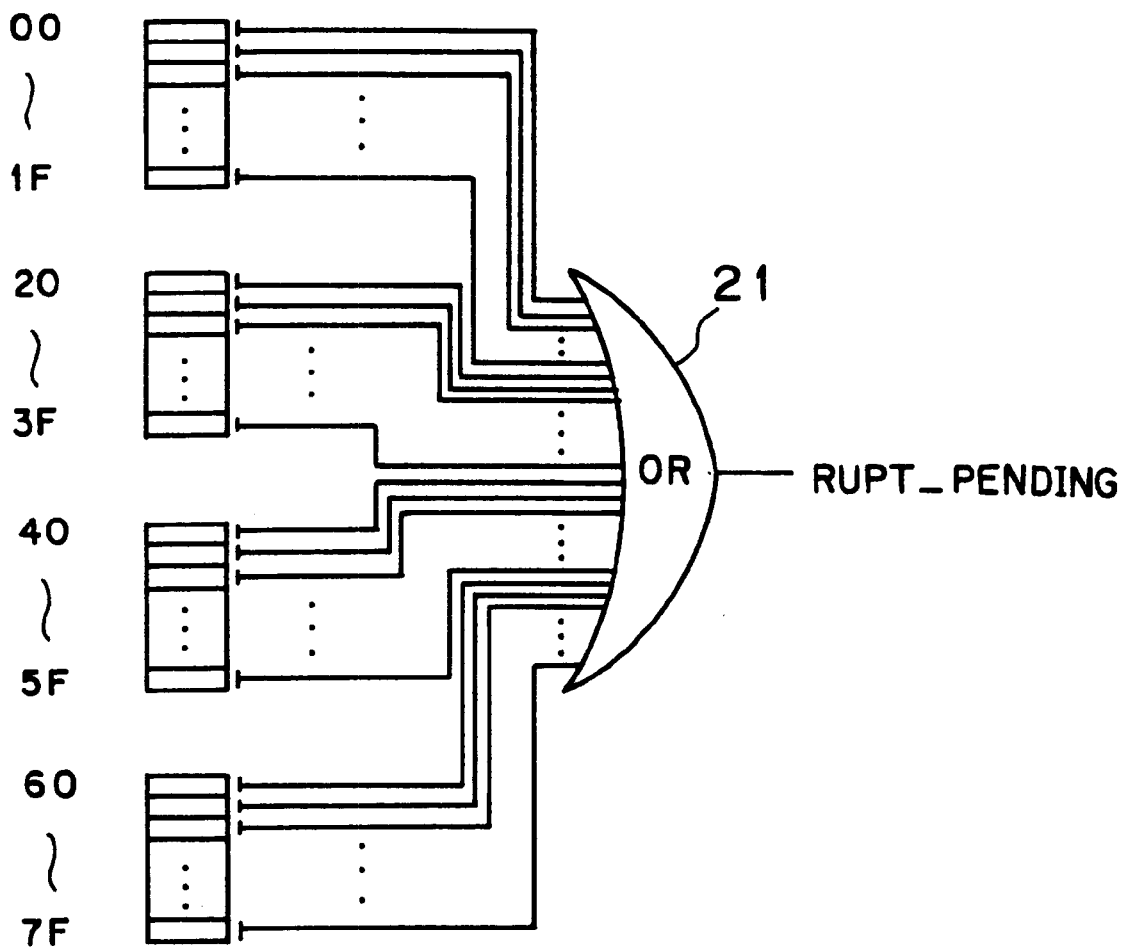
FIG. 7 exemplifies the configuration of an interrupt pending signal generating circuit.

FIG. 7 exemplifies the configuration of the interrupt pending signal generating circuit 14 shown in FIG. 5. In this figure, the contents of all of the pending latches, the 128 latches in FIG. 3 are provided to an OR gate 21. If "1" indicating the presence of a pending floating interrupt is stored in at least one of the 128 latches, the rupture pending signal output from the OR gate 21 is driven to "H".

Figure 8:
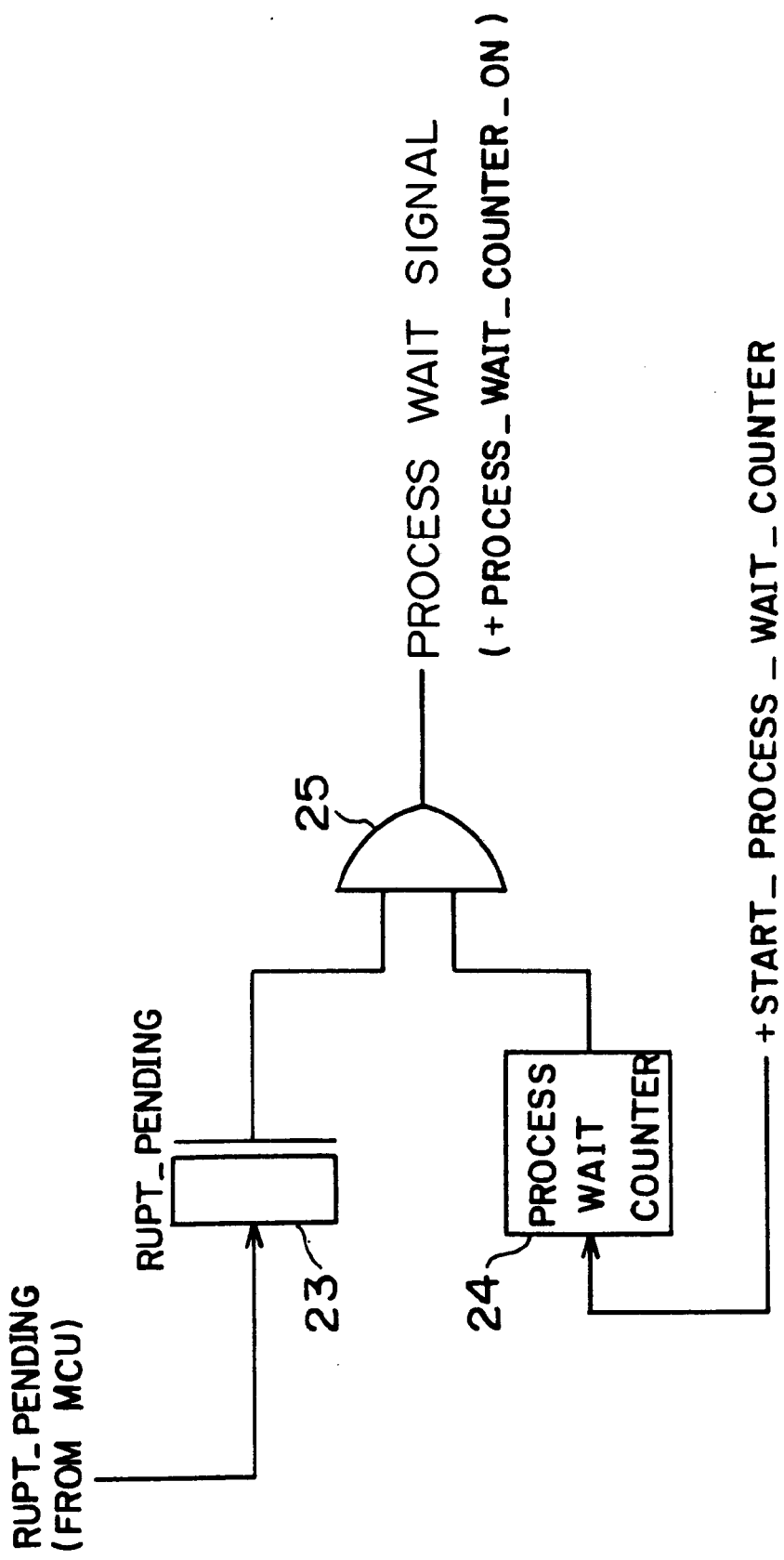
FIG. 8 exemplifies the configuration of a process wait signal generating circuit using interrupt pending information.

FIG. 8 is a block diagram showing the configuration of the process wait signal generating circuit 17 using the interrupt pending information, which is arranged within the CPU 12 shown in FIG. 5. In this figure, the process wait signal generating circuit 17 is composed of a latch 23 for storing the rupture pending signal (RUPTURE_PENDING) transmitted from the MCU 11 side shown in FIG. 5, a process wait counter 24 to which a start process wait counter signal (+START_PROCESS_WAIT_COUNTER) input from the interrupt processing controlling unit 18 when an interrupt condition change instruction is decoded is provided, and an AND gate 25 outputting a process wait signal (+PROCESS_WAIT_COUNTER_ON).

The output of the process wait counter 24 remains H while the process wait counter is running. If the value of the rupture pending signal stored in the latch 23 is "H", that is, if at least one floating interrupt is pending, the process wait counter on signal is output from the AND gate 25 until the process wait counter 24 times out. While the process wait counter signal remains "H", the process for an interrupt condition change instruction by the CPU is locked.

Figure 9:
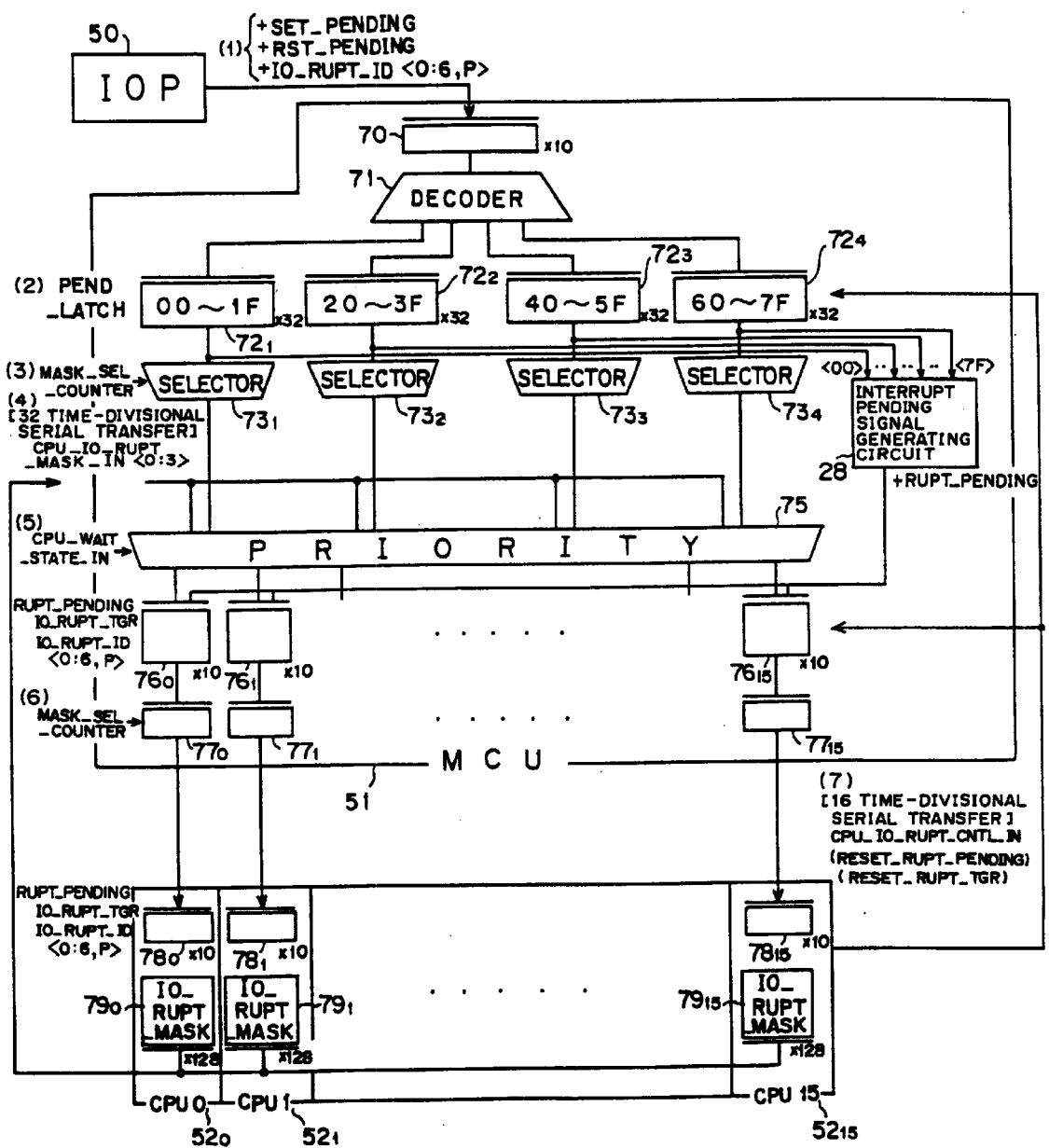
FIG. 9 is a block diagram showing the detailed configuration of the information processing device according to the first preferred embodiment.

FIG. 9 is a block diagram showing the detailed configuration of the information processing device according to the first preferred embodiment. Since this configuration is similar to that of the conventional example shown in FIG. 3, its detailed explanation is omitted here. However, there is a fundamental difference in that an interrupt pending signal generating circuit 28 is added as a portion specific to the first preferred embodiment. This circuit was explained by referring to FIG. 7. Namely, if "1" indicating the presence of a pending floating interrupt is stored in at least one of the 128 bits as the contents stored in the pending latches, "H" is output as a rupture pending signal (RUPT_PENDING). This signal is stored in the latches $76_0$ to $76_{15}$ corresponding to the respective CPUs within the MCU 11.

Accordingly, the number of bits of each of the latches $76_0$ to $76_{15}$ totals 10, because 1 bit storing the value of the rupture pending signal increases from the 9 bits shown in FIG. 3. Also the number of bits of each of the latches $78_0$ to $78_{15}$ on the CPU side, which stores the IO rupture and ID trigger signals transmitted to a selected CPU, totals 10 in order to store the value of the rupture pending signal.

Figure 10:
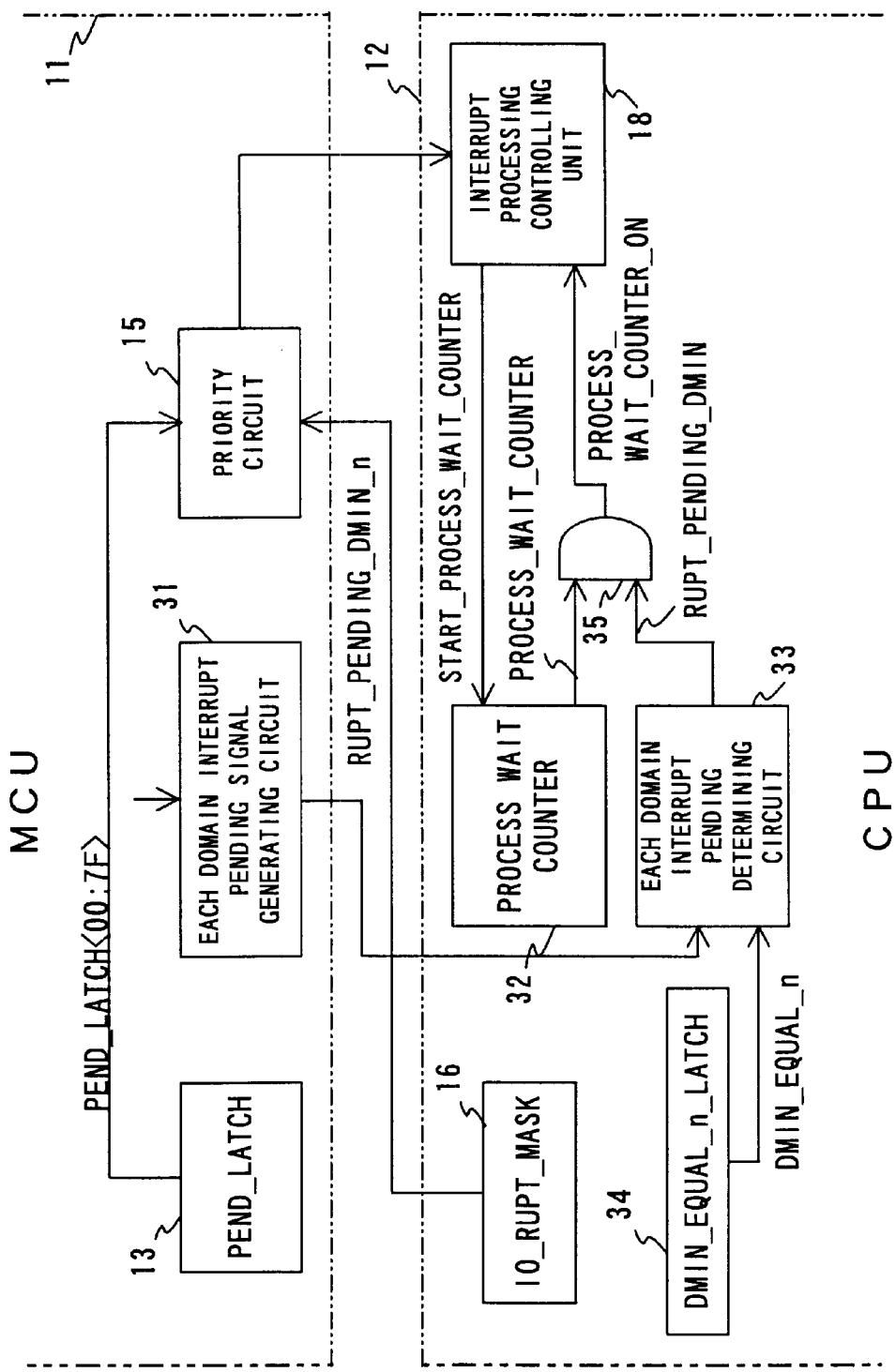
FIG. 10 is a block diagram showing the fundamental configuration of the information processing device according to the second preferred embodiment of the present invention.

FIG. 10 is a block diagram showing the fundamental configuration of the information processing device according to the second preferred embodiment. In the second preferred embodiment, a pending floating interrupt is processed when pluralities of CPUs and memory areas are allocated as domains in correspondence with processing. If a pending floating interrupt corresponds to one domain, CPUs to which other domains are allocated have nothing to do with the pending floating interrupt when an interrupt condition change instruction is issued. Therefore, the CPUs can immediately execute the interrupt condition change instruction.

Comparing FIG. 10 with FIG. 5, there are differences in that each domain interrupt pending signal generating circuit 31 is arranged as a replacement of the interrupt pending signal generating circuit within the MCU 11, and a process wait counter 32, an each domain pending interrupt determining circuit 33, a domain equal n latch 34, and an AND gate 35 are arranged as a replacement of the process wait signal generating circuit using the interrupt pending information on the CPU 12 side.

If the number of domains is "n", the each domain interrupt pending signal generating circuit 31 on the MCU side 11 generates a rupture pending domain n signal (RUPT_PENDING_DMIN_n) indicating whether or not a pending floating interrupt exists in correspondence with the respective "n" domains, and outputs the generated signal to the CPU 12 side.

On the CPU 12 side, this signal is provided to the each domain pending interrupt determining circuit 33. Also the contents stored in the domain equal n latch 34 are provided to the each domain pending interrupt determining circuit 33. This latch stores the data indicating to which domain a corresponding CPU is allocated.

The each domain pending interrupt determining circuit 33 determines whether or not a pending interrupt corresponding to the domain to which a corresponding CPU is allocated in correspondence with the inputs of these signals, and outputs a rupture pending domain signal (RUPT_PENDING_DMIN) to the AND gate 35 if such a pending interrupt exists. The AND gate corresponds to the AND gate explained by referring to FIG. 8, and the rupture pending domain signal output from the each domain pending interrupt determining circuit 33 is equivalent to the output of the latch 23.

Accordingly, the process wait counter on signal (PROCESS_WAIT_COUNTER_ON) as the output of the AND gate is driven to "H" from when the start process wait counter signal (START_PROCESS_WAIT_COUNTER) is input from the interrupt processing controlling unit 18. Then, the interrupt processing controlling unit 18 waits until a trigger signal is provided from the MCU 11 side, or until the process wait counter on signal is driven to "L" after the process wait counter 32 times out.

The process flowchart for an interrupt condition change instruction in the second preferred embodiment is fundamentally the same as that shown in FIG. 6. However, in step S2 of this process, whether or not a pending floating interrupt exists in correspondence with each domain is indicated, and whether or not a pending floating interrupt exists in correspondence with a domain to which a corresponding CPU is allocated is determined by using the signal that is always transmitted form the MCU side.

Figure 11:
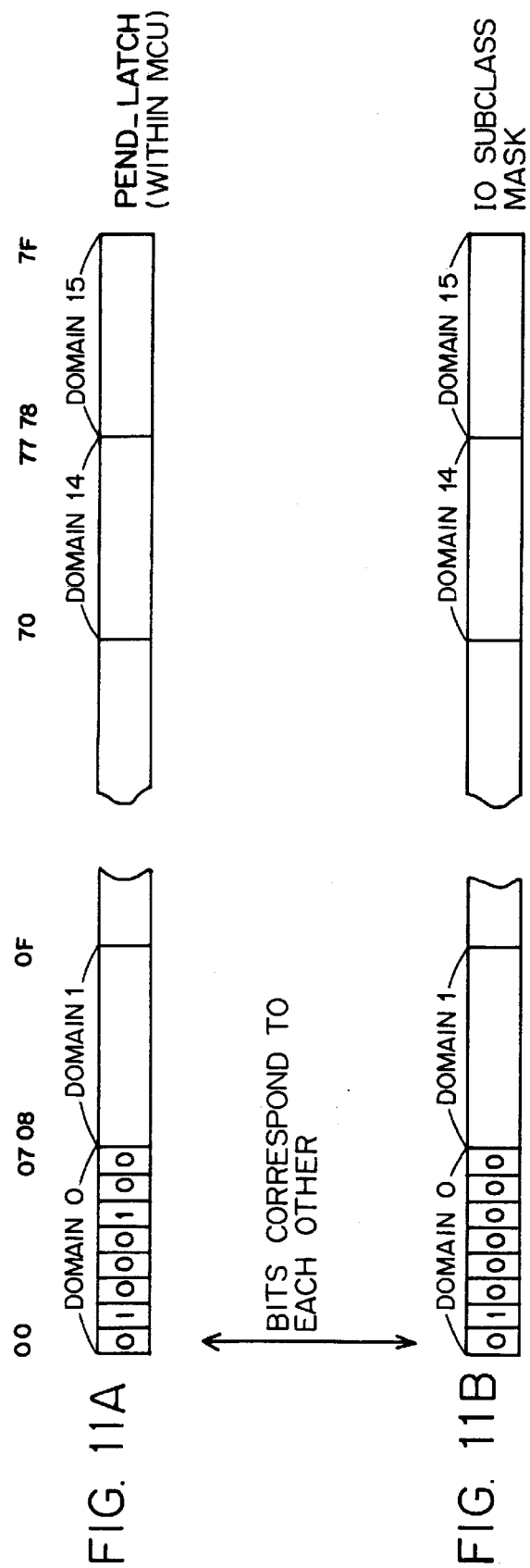
FIG. 11A exemplifies the contents stored in a pending latch.
FIG. 11B exemplifies the contents stored in an IO subclass mask as an interrupt enable mask.

FIG. 11A explains the contents stored in a pending latch in correspondence with a domain, while FIG. 11B explains an IO subclass mask as an interrupt enable mask. FIG. 11A exemplifies the contents stored in the pending latch, and shows that there are 128 subclasses (8 for each domain) as logical input/output paths corresponding to, for example, the 128 input/output channels as explained by referring to FIG. 3. In the meantime, FIG. 11B exemplifies the contents stored in the IO subclass mask as an interrupt enable mask.

The IO subclass mask is intended to indicate whether or not an interrupt is enabled for a corresponding subclass, or to determine the priority of an interrupt request in its domain. In FIG. 11B, the bit for a subclass 1 is "1" in correspondence with a domain "0", which indicates that an interrupt is enabled for this subclass, or an interrupt priority is given to this subclass. By way of example, in FIG. 3, the IO processor indicates to which subclass in which domain an IO interrupt corresponds by using the IO rupture ID (7 bits), and transmits this information to the MCU 51.

Figure 12:
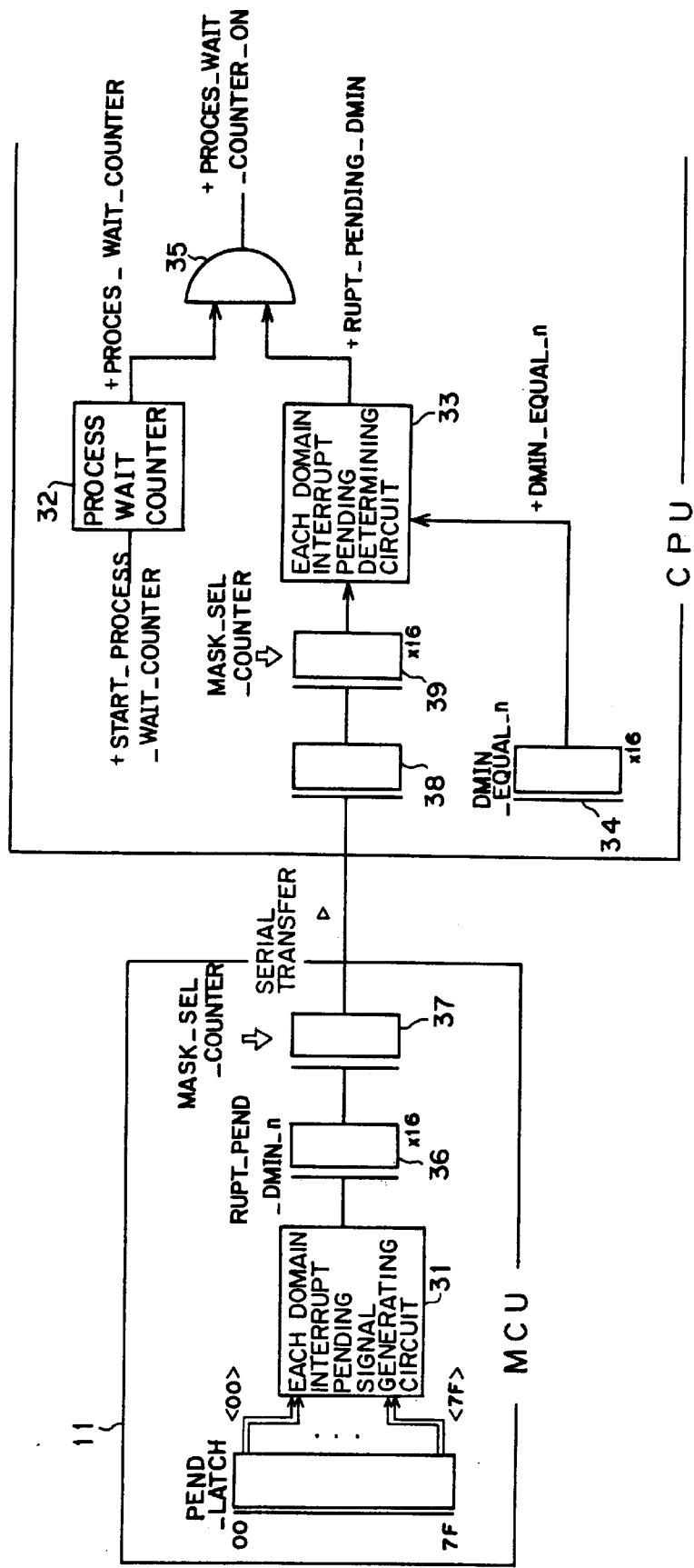
FIG. 12 is a schematic diagram explaining the method processing a pending interrupt in the second preferred embodiment.

FIG. 12 is a schematic diagram explaining the IO interrupt processing method using each domain interrupt pending information. In this figure, the rupture pending domain n signal that the each domain interrupt pending signal generating circuit 31 generates from the contents stored in a pending latch on the MCU 11 side is serially transferred, for example, in 16 time divisions to the CPU side. This serial transfer is similar to that shown in FIG. 3.

On the CPU 12 side, the each domain interrupt pending signal and the rupture pending domain n signal, which are transmitted from the MCU 11 side, are stored in a latch 39 via a latch 38. Its stored contents are provided to the each domain pending interrupt determining circuit 33 along with the contents stored in the domain equal n latch 34 in a similar manner as in FIG. 10. While its output remains "H", the process wait counter on signal output from the AND gate 35 continues to be "H" in a similar manner as in FIG. 10.

FIG. 13 exemplifies the configuration of the each domain interrupt pending signal generating circuit. In this figure, the contents of the 8 bits of the respective pending latches are provided to OR gates $41_0$ to $41_{15}$ in correspondence with the 16 domains as explained by referring to FIG. 11, and the rupture pending domain signal corresponding to each of the domains 0 to 15 is output.

Figure 14:
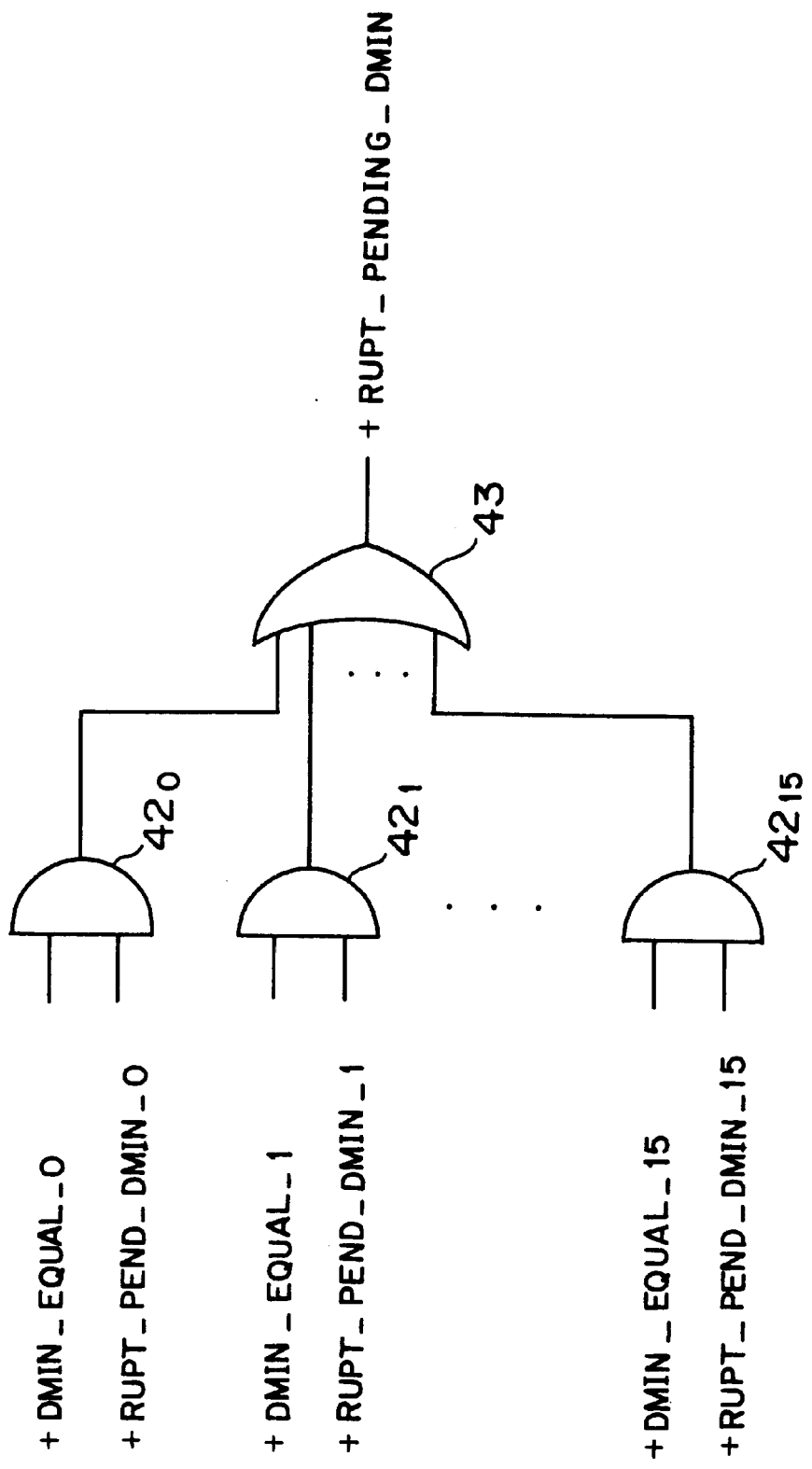
FIG. 14 exemplifies the configuration of an each domain pending interrupt determining circuit.

FIG. 14 exemplifies the configuration of the each domain pending interrupt determining circuit. In this figure, the determining circuit is composed of AND gate $42_0$ to $42_{15}$, to one of whose input terminals the rupture pending domain signal corresponding to each of the domains 0 to 15 output from each of the OR gates $41_0$ to $41_{15}$, shown in FIG. 13 is input, to the other of whose input terminals the signal indicating to which domain a corresponding CPU is allocated as the output of the domain equal n latch 34 is input, and an OR gate 43 to which the outputs of these AND gates are input.

As described above, the domain equal n latch 34 is a latch holding the data indicating to which domain a corresponding CPU is allocated. Assuming that the corresponding CPU is allocated to a domain 0, the domain equal 0 signal (+DMIN_EQUAL_0) input to the AND gate $42_0$ is driven to "H". If the rupture pending domain 0 signal (+RUPT_PEND_DMIN_0) indicating that the floating interrupt corresponding to the domain 0 is pending is "H" at this time, the outputs of the AND gate $42_0$ and the OR gate 43 are driven to "H", so that the rupture pending domain signal output from the OR gate 43, that is, the signal indicating that the floating interrupt is pending in correspondence with the domain to which a corresponding CPU is allocated is driven to "H".

Figure 15:
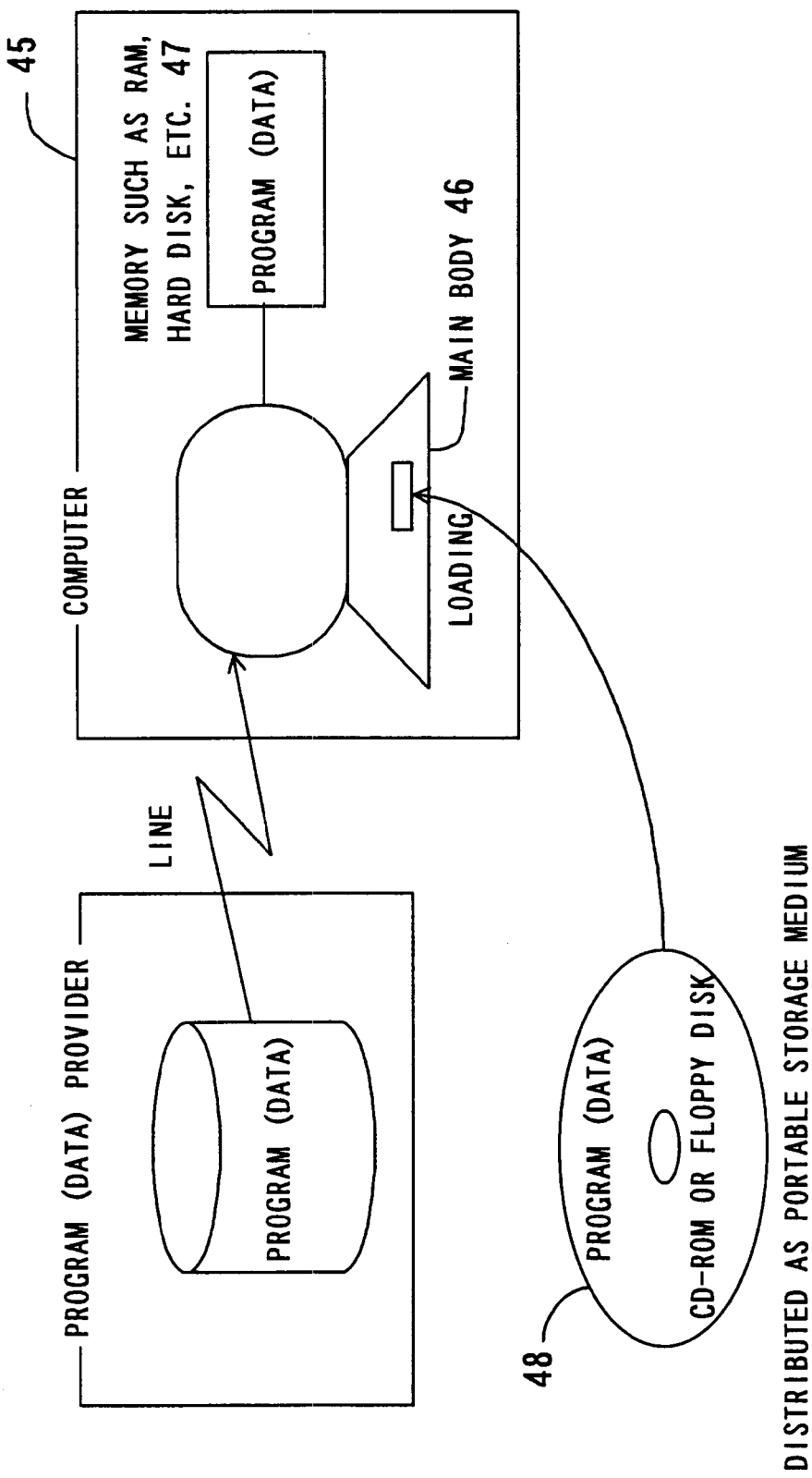
FIG. 15 is a schematic diagram explaining the loading of programs for implementing the present invention into a computer.

Explained last is the loading of programs such as an interrupt condition change process, etc. according to the present invention into a computer, by referring to FIG. 15. In this figure, a computer 45 is composed of a main body 46 and a memory 47. The main body 46 is assumed to comprise the above described plurality of CPUs, MCU (Memory Control Unit), etc.

The programs, etc. used in the above described first and second preferred embodiments (see FIG. 6) are stored in the memory 47. The programs are executed by the main body 46, so that, for example, an interrupt condition change instruction is executed.

As the memory 47, memories in various forms such as a RAM (Random Access Memory), a hard disk, an optical disk, a magneto-optical disk, etc. can be used.

These programs may be stored in a portable storage medium 48, and executed by being loaded into the computer 45, or by being transmitted from a program provider side via a line 49 and loaded into the computer 45. As the portable storage medium 48, marketed storage media in various forms such as a floppy disk, a CD-ROM, an optical disk, a magneto-optical disk, etc. can be used.

As described above in detail, according to the present invention, if no pending floating interrupts exist when an interrupt condition change instruction is issued, a CPU can immediately execute this instruction. Additionally, domains are allocated to respective CPUs. Therefore, even if a pending floating interrupt is not the one corresponding to the domain to which a corresponding CPU is allocated, an interrupt condition change instruction can be immediately executed, which greatly contributes to the improvement of the performance of an information processing device.

What is claimed is:

1. An information processing device that comprises a plurality of CPUs, and can make a floating interrupt as an interrupt which can be executed by any of the plurality of CPUs pending, comprising:
    an interrupt pending signal generating unit always transmitting a signal which indicates a presence/absence of a pending floating interrupt to the plurality of CPUs; and
    an interrupt condition change instruction execution controlling unit, which is comprised by each of the plurality of CPUs, making its own CPU execute an interrupt condition change instruction, when the interrupt condition change instruction is issued, and an output of said interrupt pending signal generating unit indicates the absence of a pending interrupt.

2. An information processing device that comprises a plurality of CPUs to which domains corresponding to processing are respectively allocated, and can make a floating interrupt as an interrupt which can be executed by any of the plurality of CPUs pending, comprising:
    an each domain interrupt pending signal generating unit always transmitting a signal indicating a presence/absence of a pending floating interrupt to the plurality of CPUs in correspondence with the respective domains; and
    a pending interrupt determining unit, which is comprised by each of the CPUs, determining a presence/absence of a pending floating interrupt corresponding to a domain to which its own CPU is allocated by using the signal from said each domain interrupt pending signal generating unit.

3. The information processing device according to claim 2, wherein
    each of the plurality of CPUs further comprises an interrupt condition change instruction execution controlling unit immediately making its own CPU execute an interrupt condition change instruction, when the interrupt condition change instruction is issued and said pending interrupt determining unit determines the absence of a pending interrupt for a domain to which its own CPU is allocated.

4. An interrupt condition change instruction executing method for use in an information processing device which comprises a plurality of CPUs, and can make a floating interrupt as an interrupt that can be executed by any of the plurality of CPUs pending, comprising:
    receiving a signal which indicates a presence/absence of a pending floating interrupt and is always transmitted; and
    immediately executing an interrupt condition change instruction when the interrupt condition change instruction is issued and the signal indicates the absence of a pending interrupt.

5. An interrupt condition change instruction executing method for use in an information processing device that comprises a plurality of CPUs to which domains corresponding to processing are respectively allocated, and can make a floating interrupt as an interrupt which can be executed by any of the plurality of CPUs pending, comprising:
    receiving a signal which indicates a presence/absence of a pending floating interrupt in correspondence with the respective domains and is always transmitted;
    determining a presence/absence of a pending floating interrupt for a domain to which a corresponding CPU is allocated by using the received signal; and
    immediately executing an interrupt condition change instruction, when the interrupt condition change instruction is issued, and the absence of a pending interrupt for a domain to which the corresponding CPU is allocated is determined as a result of the determination.

6. A computer-readable portable storage medium on which is recorded a program for causing a computer to execute a process, for use in an information processing device that comprises a plurality of CPUs, and can make a floating interrupt as an interrupt which can be executed by any of the plurality of CPUs pending, said process comprising:
    receiving a signal which indicates a presence/absence of a pending floating interrupt and is always transmitted; and immediately executing an interrupt condition change instruction when the interrupt condition change instruction is issued and the signal indicates the absence of a pending interrupt.

7. A computer-readable portable storage medium on which is recorded a program for causing a computer to execute a process, for use in an information processing device which comprises a plurality of CPUs to which domains corresponding to processing are respectively allocated, and can make a floating interrupt as an interrupt which can be executed by any of the plurality of CPUs pending, comprising:

receiving a signal which indicates a presence/absence of a pending floating interrupt in correspondence with the respective domains and is always transmitted;

determining a presence/absence of a pending floating interrupt for a domain to which a corresponding CPU is allocated by using the received signal; and immediately executing an interrupt condition change instruction, when the interrupt condition change instruction is issued, and the absence of a pending interrupt for a domain to which the corresponding CPU is allocated is determined as a result of the determination.

8. An information processing device that comprises a plurality of CPUs, and can make a floating interrupt as an interrupt which can be executed by any of the plurality of CPUs pending, comprising:

interrupt pending signal generating means for always transmitting a signal which indicates a presence/absence of a pending floating interrupt to the plurality of CPUs; and interrupt condition change instruction execution controlling means, which is comprised by each of the plurality of CPUs, for making its own CPU execute an interrupt condition change instruction, when the interrupt condition change instruction is issued, and an output of said interrupt pending signal generating means indicates the absence of a pending interrupt.

9. An information processing device that comprises a plurality of CPUs to which domains corresponding to processing are respectively allocated, and can make a floating interrupt as an interrupt which can be executed by any of the plurality of CPUs pending, comprising:

each domain interrupt pending signal generating means for always transmitting a signal indicating a presence/absence of a pending floating interrupt to the plurality of CPUs in correspondence with the respective domains; and pending interrupt determining means, which is comprised by each of the CPUs, for determining a presence/absence of a pending floating interrupt corresponding to a domain to which its own CPU is allocated by using the signal from said each domain interrupt pending signal generating means.

* * * * *